United States Patent [19]
Cohen et al.

[11] Patent Number: 5,306,272
[45] Date of Patent: Apr. 26, 1994

[54] ADVANCER FOR SURGICAL INSTRUMENT

[75] Inventors: Donald Cohen, Irvine; John Aoki, Bellflower, both of Calif.

[73] Assignee: Neuro Navigational Corporation, Costa Mesa, Calif.

[21] Appl. No.: 970,705

[22] Filed: Nov. 2, 1992

[51] Int. Cl.⁵ .............................................. A61B 19/00
[52] U.S. Cl. .......................................... 606/1; 606/130; 403/370; 604/165
[58] Field of Search ............... 606/1, 129, 130; 403/370, 368, 367, 343; 604/165

[56] References Cited

U.S. PATENT DOCUMENTS

| | | | |
|---|---|---|---|
| 2,279,508 | 4/1942 | Bergan | 403/370 |
| 3,508,552 | 4/1970 | Hainault | 606/130 |
| 3,858,578 | 1/1975 | Milo | 128/20 |
| 4,228,799 | 10/1980 | Anichkov et al. | 606/130 |
| 4,350,159 | 9/1982 | Gouda | 606/130 |
| 4,419,094 | 12/1983 | Patel | 604/165 |
| 4,465,069 | 8/1984 | Barbier et al. | 606/130 |
| 4,706,665 | 11/1987 | Gouda | 606/130 |

*Primary Examiner*—Tamara L. Graysay
*Attorney, Agent, or Firm*—John L. Rogitz

[57] ABSTRACT

A device for axially advancing a surgical instrument into the brain of a patient includes an advancer that is engageable with the gooseneck of a surgical apparatus. The is axially telescoping, and the advancer can selectively grip the surgical instrument. Accordingly, the surgical instrument can be gripped by the advancer and the advancer telescoped to advance the instrument into the brain along a predetermined path.

17 Claims, 2 Drawing Sheets

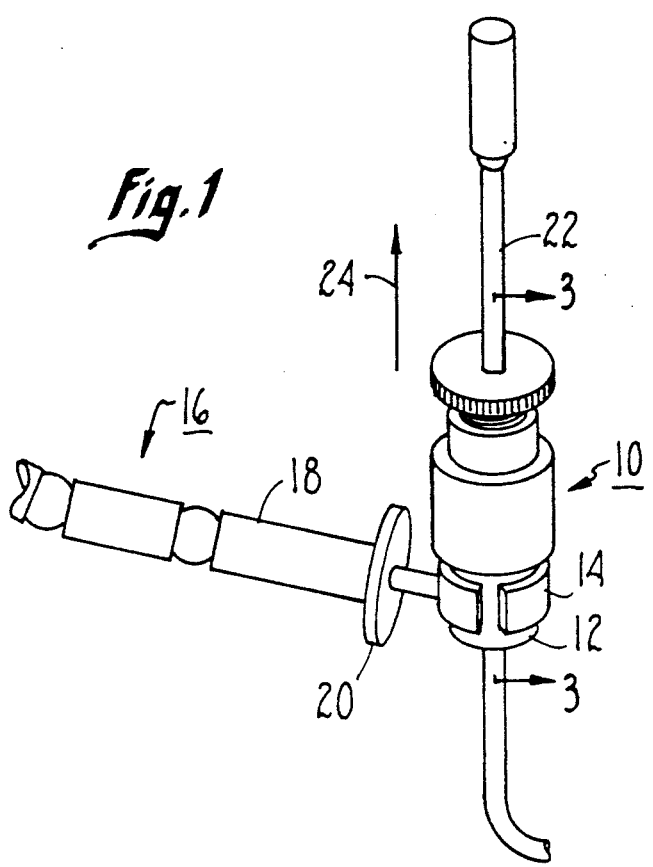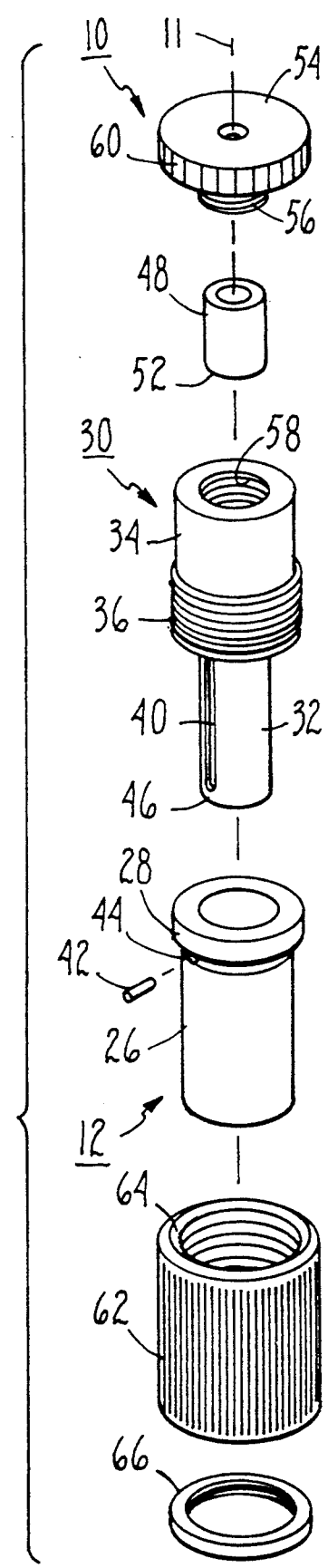

ADVANCER FOR SURGICAL INSTRUMENT

FIELD OF THE INVENTION

The present invention relates generally to neurosurgery instruments, and more particularly to devices for advancing neurosurgery probes into a patient.

BACKGROUND

To perform neurosurgery, it is typically necessary to advance a neurosurgical instrument, e.g., an endoscope, scalpel, etc. into the brain of a patient. The instrument is advanced into the brain until the operable portion of the instrument is positioned adjacent the site of interest, i.e., the site of the brain to be operated on. Then, the instrument is manipulated as appropriate for performing the particular procedure.

Modern neurosurgery techniques fall into two general categories. The first is relatively invasive and involves removing a large portion of the patient's skull, to gain access to the brain. After surgery, the portion of the skull which was removed is replaced.

The second type of neurosurgery, referred to herein as neuroendoscopy because it often permits advancing an endoscope into the brain to provide the surgeon with a view of the brain, is much less traumatic to the patient than the first. Neuroendoscopy requires drilling a small hole in the skull, and then advancing one or more surgical instruments and/or endoscopes through the hole into the brain to perform the operation. Neuroendoscopy is preferred when use of it is practicable, for the reason that it causes relatively little trauma to the patient and allows for relatively rapid patient recovery.

Not surprisingly, in neuroendoscopy the surgical instrument or instruments must be advanced along a precisely determined path into the brain, to avoid unintentionally damaging the brain. Also, once precisely positioned in the brain, the instruments must be securely held in position, again to avoid unintentional injury to the brain.

To aid the surgeon in advancing an instrument or probe along a precisely predetermined path, devices referred to as stereotactic frames have been introduced. A stereotactic frame can be positioned near the patient's skull prior to surgery, and the frame has one or more surgical instrument holders, each of which can securely grip a surgical instrument or probe and hold the probe in a predetermined orientation relative to the brain.

One type of stereotactic device is the Bookler Laparascopic Scope Holder made by Flex-Bar Machinery Corporation of New York. The Bookler Scope Holder has a flexible arm that has a fixed end which is mounted on a frame. The flexible arm, sometimes referred to as a gooseneck, has a free end, and the free end can be moved in any direction in three dimensional space relative to the frame, and can be locked relative to the frame once the free end has been placed in the desired position and orientation relative to the frame.

A neurosurgery instrument holder is connected to the free end of the gooseneck, such that a neurosurgery instrument can be engaged with the holder of the gooseneck. The instrument can thus be oriented relative to the frame as desired. To orient the instrument relative to the frame, the free end is unlocked, the instrument moved as desired, and the free end locked again in position.

It can be appreciated in reference to the above discussion that once a neurosurgery instrument has been engaged with the holder of the gooseneck and oriented as desired, the free end of the gooseneck must be unlocked to permit advancing the instrument along the predetermined path. Unlocking the free end, however, as discussed above, permits movement of the instrument in all three spatial dimensions.

This is undesirable, because it results in difficulty in simply advancing the instrument axially into the brain, while maintaining the orientation of the instrument relative to the brain. Stated differently, each time it is desired to move the instrument axially into the brain along the predetermined path, the free end of the gooseneck must be unlocked, permitting unintentional movement of the instrument in the remaining two dimensions and potentially causing the instrument to deviate from the predetermined path of advancement.

Accordingly, it is an object of the present invention to provide a device for permitting movement, in only a single direction, of a surgical instrument that is held by a surgical apparatus. Another object of the present invention is to provide an adaptor for engaging the holder of the flexible arm of a surgical apparatus and for selectively gripping a surgical instrument. Another object of the present invention is to provide an adaptor for connecting a surgical instrument to a surgical apparatus, that is easy to use and cost-effective to manufacture.

SUMMARY OF THE INVENTION

A device is disclosed which is engageable with a surgical apparatus for axially advancing a surgical instrument into a patient. The device of the present invention includes a telescoping advancer which is engageable with the surgical apparatus. As intended by the present invention, the advancer is movable from a shortened configuration, wherein the advancer has a first length, to an extended configuration, wherein the advancer has a second length longer than the first. The advancer includes a gripping element for gripping the surgical instrument, such that the surgical instrument is advanced axially into the patient when the advancer is moved toward the extended configuration.

In another aspect of the present invention, an axial advancer for advancing a neurosurgery instrument into the brain of a patient includes an annular adaptor for engaging a surgical apparatus. The adaptor defines an axis, and a hollow holder is slidably disposed in the adaptor coaxially with the adaptor.

Also, an annular resilient gripping element is disposed in the holder coaxially with the holder. In accordance with the present invention, the gripping element is biased to a normal configuration, wherein the gripping element has a first inside diameter that is sufficiently large to permit the surgical instrument to be positioned within the gripping element. Additionally, the gripping element has a gripping configuration, wherein the gripping element has a second inside diameter smaller than the first, for gripping the surgical instrument.

Further, a cap is threadably engaged with the holder for selectively moving the gripping element to the gripping configuration to grip a surgical instrument. Moreover, a handle is threadably engaged with the holder and is rotatably engaged with the adaptor for selectively moving the holder axially relative to the adaptor. When the surgical instrument is gripped by the gripping element and the handle is rotated in a predetermined direction, the surgical instrument is axially advanced into the patient's brain.

Preferably, the holder is formed with a seat, and the cap can be rotated to urge the gripping element against the seat and thereby move the gripping element to the gripping configuration. Also, the holder has a longitudinal slot formed in it, and the advancer includes a retaining pin which is attached to the adaptor and which protrudes through the slot to retain the holder within the adaptor.

As further intended by the present invention, the holder has an inner surface and an outer surface, and a portion of the inner surface is threaded for engaging the cap. Further, a portion of the outer surface of the holder is threaded for engaging the handle.

In the presently preferred embodiment, the adaptor is configured for engaging an instrument holder on a flexible arm of a surgical apparatus.

In another aspect of the present invention, a device for moving a surgical instrument axially relative to a surgical apparatus has an adaptor for engaging the surgical apparatus and a holder slidably disposed in the adaptor. Also, the device has a gripping element that is disposed in the holder and is selectively movable between a normal configuration, wherein the gripping element does not grip the surgical instrument, and a gripping configuration, wherein the gripping element can hold the surgical instrument stationary relative to the holder.

In yet another aspect of the present invention, a method is disclosed for axially advancing a neurosurgery instrument into the brain of a patient along a predetermined path. The method of the present invention includes the steps of providing a surgical apparatus which is positionable in a predetermined orientation relative to the brain. Also, an advancer is provided which has an extended configuration and a shortened configuration, and the advancer holds the instrument.

In accordance with the method of the present invention, the advancer is engaged with the surgical apparatus, and the surgical instrument is engaged with the advancer such that the surgical instrument is oriented along the predetermined path of advancement into the brain. The advancer can then be moved toward the extended configuration to advance the instrument into the brain along the predetermined path.

The details of the present invention, both as to its construction and operation, can best be understood in reference to the accompanying drawings, in which like numerals refer to like parts, and which:

BRIEF DESCRIPTION OF THE DRAWINGS

FIG. 1 is a perspective view of the advancer for neurosurgery probe of the present invention, shown in operable engagement with a surgical apparatus and a surgical instrument, with the advancer in the shortened configuration and with portions of the surgical instrument and surgical apparatus broken away;

FIG. 2 is an exploded isometric view of the advancer for neurosurgery probe of the present invention;

DETAILED DESCRIPTION OF THE PREFERRED EMBODIMENT

Figure 3:
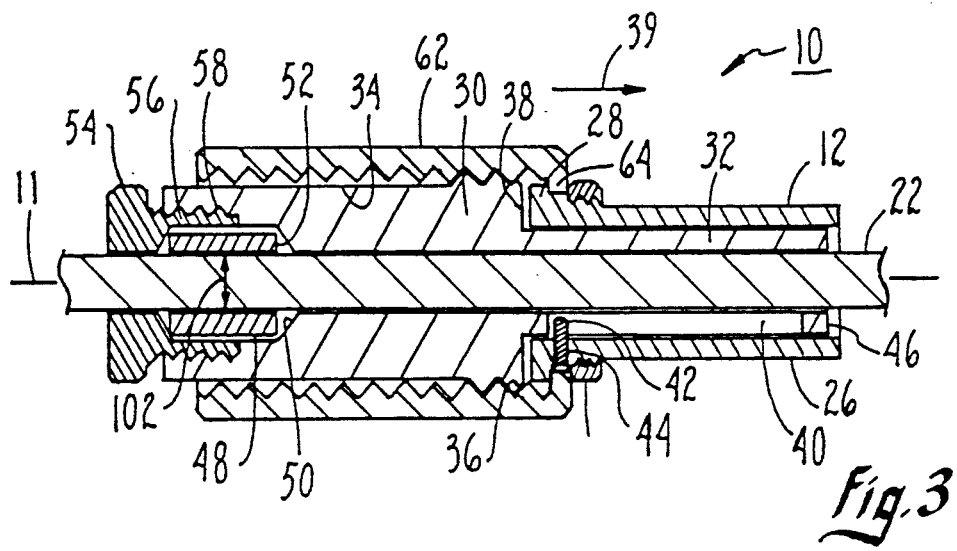
FIG. 3 is a cross-sectional view of the advancer for neurosurgery probe of the present invention, as seen along the line 3—3 in FIG. 1.

Referring initially to FIG. 1, an advancer for axially advancing a surgical instrument into a patient is shown, generally designated 10. As shown, the advancer 10 has a generally cylindrical adaptor 12 that can fit snugly within an annular holder 14 of a surgical apparatus, generally designated 16. Preferably, the advancer 10 is made of a rigid, lightweight, low-friction hard plastic or metal material. More preferably, the advancer 10 is made of anodized aluminum, polycarbonate, or steel, and can be made by machining or molding processes well-known in the art.

In one presently preferred embodiment, the surgical apparatus 16 is a Bookler Laparascopic Scope Holder made by Flex-Bar Machinery Corporation of New York. Such an apparatus includes a flexible arm 18 (familiarly referred to as a gooseneck) having a free end 20, and the free end 20 can be moved in space to orient the holder 14 as desired. Also, the arm 18 can be locked to prevent motion of the free end 20.

FIG. 1 further shows that the advancer 10 can hold a surgical instrument 22. In one presently preferred embodiment, the surgical instrument 22 is a neuroendoscope. It is to be understood that the surgical instrument 22 can be another type of surgical instrument, e.g., a probe, an endoscopic scalpel or forceps, etc.

In accordance with the principles of operation of a Bookler Laparascopic Scope Holder, the arm 18 can be moved as appropriate to orient the holder 14 as desired to establish a predetermined path of advancement of the surgical instrument 22 into a patient, e.g., into the brain of a patient incident to neurosurgery. As will be more fully appreciated after further discussion below, the advancer 10 can telescope axially to advance the surgical instrument 22 into the patient (i.e., in the direction of the arrow 24), without requiring the unlocking of the arm 18 of the surgical apparatus 16.

Now referring to FIGS. 2 and 3, the details of the advancer 10 can be seen. As shown in FIGS. 2 and 3, the components of the advancer 10 described below are coaxial, i.e., all the hollow or annular components described below share a common axis 11.

FIGS. 2 and 3 show that the advancer 10 includes the adaptor 12, and the adaptor 12 has a hollow cylindrical adaptor skirt 26 and an annular flange 28 formed integrally with the adaptor skirt 26. The adaptor skirt 26 is configured to fit snugly within the holder 14 (FIG. 1) in an interference fit therewith.

FIGS. 2 and 3 further show that the advancer 10 includes a hollow instrument holder 30. Preferably, the instrument holder 30 is made of a unitary piece of rigid material. The instrument holder 30 has a hollow cylindrical holder skirt 32 which can slide within the adaptor 12. Also, the instrument holder 30 has a hollow cylindrical engagement segment 34 that has a larger outside diameter than the holder skirt 32, and a portion 36 of the outer surface of the engagement segment 34 is threaded.

As intended by the present invention, slidable motion of the instrument holder 30 within the adaptor 12 is mechanically limited by the structure described below. More specifically, as shown best in FIG. 3, a face 38 of the engagement segment 34 of the instrument holder 30 can abut the adaptor flange 28, to prevent movement of the face 38 past the flange 28 in the direction of the arrow 39 in FIG. 3. Additionally, FIGS. 2 and 3 show that a slot 40 is formed longitudinally in the holder skirt 32, and a retainer pin 42 extends into the slot 40. As shown, the retainer pin 42 is fixedly mounted in an orifice 44 that is formed in the adaptor 12. The pin 42 can abut a stop 46 that is formed on the instrument holder 30, to prevent motion of the pin 42 past the stop 46 in the direction opposite that indicated by the arrow 39. To hold the pin 42 within the orifice 44, the pin 42 can be threaded or glued to the adaptor 12. The pin 42 also prevents rotation of the instrument holder 30 so that the holder 30 will not rotate as is axially advances (i.e., as it undergoes longitudinal translation).

Still referring to FIGS. 2 and 3, the advancer 10 includes a hollow, resilient cylindrical gripping element 48. Preferably, 180 the gripping element 48 is a compressible gland seal made of silicon or other rubber material.

As shown, the engagement segment 34 has a seat 50, and an end 52 of the gripping element 48 abuts the seat 50. As will be more fully disclosed below, when the end 52 of the gripping element 48 is urged against the seat 50, the gripping element is deformed to enable the gripping element 48 to hold the surgical instrument 22 stationary with respect to the instrument holder 30.

To provide for urging the gripping element 48 against the seat 50, compression element e.g., a hollow cap 54 is threadably engaged with the engagement segment 34 of the instrument holder 30. More specifically, an outside surface 56 of the cap 54 is threaded, and the surface 56 is threadably engaged with a threaded portion 58 of the inside surface of the engagement segment 34. Accordingly, the cap 54 can be rotated as appropriate to urge the gripping element 48 against the seat 50 and thereby deform the gripping element 48. FIG. 2 best shows that the cap 54 includes an annular cap flange 60 that is manually grippable by a person, for manipulating the cap 54.

Figure 4:
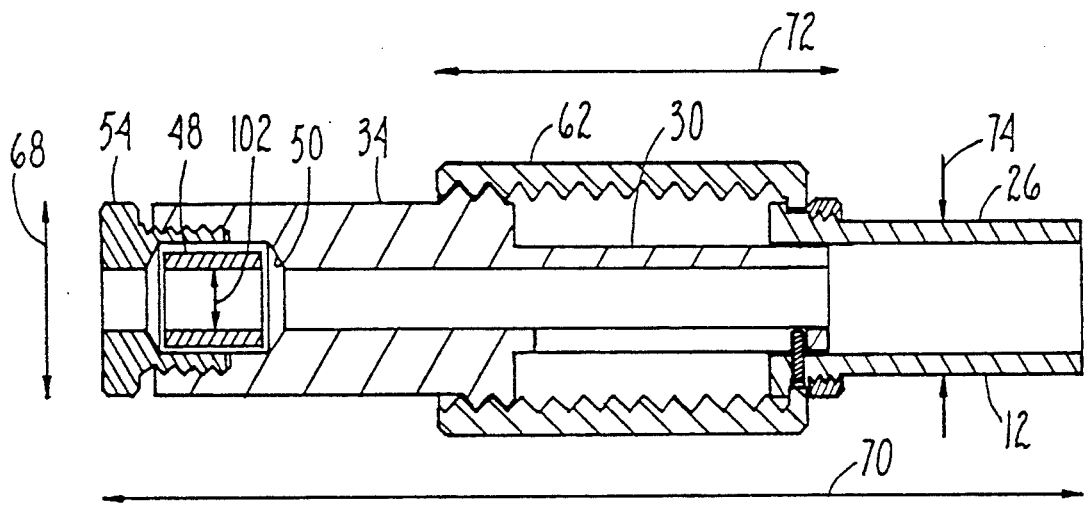
FIG. 4 is a cross-sectional view of the advancer for neurosurgery probe of the present invention, with the advancer in the extended configuration and the gripping element in the normal configuration.

Briefly cross-referencing FIGS. 3 and 4, the gripping element 48 is biased to a normal configuration (FIG. 4) when the element 48 is not urged against the seat 50. In the normal configuration, the gripping element 48 has an inside diameter $ID_1$ which is sufficiently large to permit the surgical instrument 22 (not shown in FIG. 4) to slide within the instrument holder 30.

On the other hand, when the gripping element 48 is urged against the seat 50 by the cap 54 (FIG. 3), the gripping element 48 is deformed into a gripping configuration, wherein at least a portion of the gripping element 48 has an inside diameter $ID_2$ that is sufficiently small to prevent motion of the surgical instrument 22 within the instrument holder 30.

In other words, when the gripping element 48 is in the gripping configuration, the gripping element 48 grips the surgical instrument 22 and holds it stationary with respect to the instrument holder 30. Thus, the inside diameter $ID_1$ of the gripping element 48 when in the normal configuration is greater than the inside diameter $ID_2$ of the gripping element 48 when in the gripping configuration.

Referring back to FIGS. 2 and 3, the advancer 10 includes an annular adjustment handle 62. As shown, the outside surface of the handle 62 is knurled or textured to facilitate manipulation of the handle 62 by a person. Also, the inside surface of the handle 62 is threaded, and the inside surface of the handle 62 is threadably engaged with the threaded portion 36 of the instrument holder 30.

FIGS. 2 and 3 show that the handle 62 is formed with a lip 64 that protrudes radially inwardly. A retainer ring 66 is threadably engaged with the adaptor 12, and the lip 64 of the handle 62 is positioned between the retainer ring 66 and the flange 28 of the adaptor 12. Accordingly, the handle 62 can be rotated relative to the adaptor 12, but cannot move axially relative to the adaptor 12.

As stated above, the hollow or annular components described above are coaxial, and together establish a passageway in which the surgical instrument 22 (FIGS. 1 and 3) can be positioned. It may now be appreciated that the gripping element 48 can be deformed to grip the surgical instrument 22, and the handle 62 rotated to move the instrument holder 30 from a first position (FIG. 3) to a second position (FIG. 4) relative to the adaptor 12. Stated differently, the handle 62 can be rotated to move the advancer 10 from a shortened configuration (FIG. 3) toward an extended configuration (FIG. 4) to thereby advance the surgical instrument 22 into a patient, without manipulating the arm 18 of the surgical apparatus 16.

FIG. 4 shows the dimensions of one presently preferred embodiment of the advancer 10. As shown, the cap 54 has a diameter 68 of about an inch (1.0"), and the advancer 10 has an overall length 70 of about three and six-tenths inches (3.6") when in the extended configuration. Also, the handle 62 has a length 72 of about one and three-tenths inches (1.3"), and the adaptor skirt 26 has an outside diameter 74 of about six hundred ninety-five thousandths of an inch (0.695").

Figure 5:
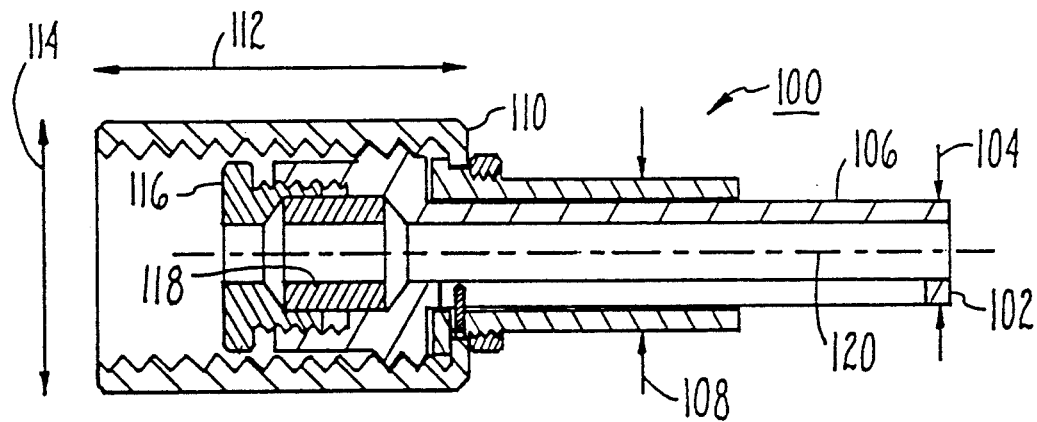
FIG. 5 is a cross-sectional view of an alternate embodiment of the advancer for neurosurgery probe of the present invention, with the gripping element in the normal configuration and the surgical instrument removed.

FIG. 5 shows an alternate embodiment of the advancer of the present invention, generally designated 100. The advancer 100 is in all essential respects identical to the advancer 10, with the exceptions shown in the drawings and noted below. Specifically, the advancer 100 has a surgical instrument holder 102 that has an outside diameter 104 of about thirty five hundredths of an inch (0.35"). Also, the advancer 100 has an adaptor 106 which has an outside diameter 108 of about fifty hundredths of an inch (0.50").

Furthermore, the advancer 100 includes a handle 110 having a length 112 of about one and two-tenths inches (1.2") and an outside diameter 114 of about eighty-eight hundredths of an inch (0.88"). As shown, the advancer 100 also has a cap 116 for compressing a gripping element 118, and the cap 116 can slide within the handle 110. Like the hollow components of the advancer 10, the hollow components of the advancer 100 share a common axis 120.

While the particular advancer for surgical instrument as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims.

What is claimed is:

1. An axial advancer, comprising:

an annular adaptor for engaging a surgical apparatus, the adaptor defining an axis;

a hollow holder slidably disposed in the adaptor in a coaxial relationship therewith;

an annular resilient gripping element disposed in the holder in a coaxial relationship therewith, the gripping element being biased to a normal configuration, wherein the gripping element has a first inside diameter, the gripping element also having a gripping configuration, wherein the gripping element has a second inside diameter smaller than the first;

a cap threadably engaged with the holder for selectively moving the gripping element to the gripping configuration; and a handle threadably engaged with the holder and rotatably engaged with the adaptor for selectively moving the holder axially relative to the adaptor.

2. The advancer of claim 1, wherein the holder is formed with a seat, and the cap can be rotated to urge the gripping element against the seat and thereby move the gripping element to the gripping configuration.

3. The advancer of claim 2, wherein the holder has a longitudinal slot formed therein, and the advancer further comprises a retaining pin attached to the adaptor and protruding through the slot to retain the holder within the adaptor.

4. The advancer of claim 3, wherein the adaptor is configured for engaging an instrument holder on a flexible arm of a surgical apparatus.

5. The advancer of claim 4, wherein the holder has an inner surface and an outer surface, and a portion of the inner surface is threaded for engaging the cap.

6. The advancer of claim 5, wherein a portion of the outer surface of the holder is threaded for engaging the handle.

7. A device for moving a surgical instrument axially relative to a surgical apparatus, comprising:

an adaptor for engaging the surgical apparatus;
a holder slidably disposed in the adaptor;
means for preventing rotation of the holder relative to the adaptor;
a gripping element made of a resilient material, the element being disposed in the holder and selectively movable between a normal configuration, wherein the gripping element does not grip the surgical instrument, and a gripping configuration, wherein the gripping element can hold the surgical instrument stationary relative to the holder; and
deforming means associated with the holder for deforming the gripping element to move the gripping element to the gripping configuration.

8. The device of claim 7, wherein the adaptor defines an axis, and the holder and the gripping element are hollow and are positioned in a coaxial relationship with the adaptor.

9. The device of claim 8,
wherein the deforming means is a cap threadably engaged with the holder for selectively moving the gripping element to the gripping configuration; and
a handle threadably engaged with the holder and rotatably engaged with the adaptor for selectively moving the holder axially relative to the adaptor.

10. The device of claim 9, wherein the holder is formed with a seat, and the cap can be rotated to urge the gripping element against the seat and thereby move the gripping element to the gripping configuration.

11. The device of claim 10, wherein said means for preventing rotation includes the holder has a longitudinal slot formed therein, and a retaining pin attached to the adaptor and protruding through the slot to retain the holder within the adaptor.

12. The device of claim 11, wherein the adaptor is configured for engaging an instrument holder on a flexible arm of a surgical apparatus.

13. The device of claim 12, wherein the holder has an inner surface and an outer surface, and a portion of the inner surface is threaded for engaging the cap, and a portion of the outer surface of the holder is threaded for engaging the handle.

14. A method for axially advancing a neurosurgery instrument into the rain of a patient along a predetermined path, comprising the steps of:

(a) providing a surgical apparatus positionable in a predetermined orientation relative to the brain;
(b) providing an advancer having an extended configuration and a shortened configuration, wherein the advancer includes a resilient gripping element;
(c) forming the gripping element to hold the neurosurgery instrument;
(d) engaging the advancer with the surgical apparatus;
(e) engaging the surgical instrument with the gripping element of the advancer such that the surgical instrument is oriented along the predetermined path of advancement into the brain; and
(f) moving the advancer toward the extended configuration to advance the instrument into the brain along the predetermined path.

15. A device engageable with a surgical apparatus for axially advancing a surgical instrument into a patient, comprising:

a telescoping advancer engageable with the surgical apparatus, the advancer being movable from a shortened configuration, wherein the advancer has a first length, to an extended configuration, wherein the advancer has a second length longer than the first, the advancer further comprising;
a resilient gripping element for gripping the surgical instrument, such that the surgical instrument can be advanced axially into the patient when the advancer is moved toward the extended configuration; and
a compression element operatively engaged with the gripping element for selectively causing the gripping element to grip the surgical instrument.

16. The device of claim 15, wherein the gripping element has a normal configuration, wherein the gripping element has a first inside diameter, the gripping element also having a gripping configuration, wherein the gripping element has a second inside diameter smaller than the first.

17. The device of claim 16, wherein the advancer includes:

an annular adaptor for engaging a surgical apparatus, the adaptor defining an axis;
a hollow holder slidably disposed in the adaptor in a coaxial relationship therewith;
a cap threadably engaged with the holder wherein the cap is the compression element; and
a handle threadably engaged with the holder and rotatably engaged with the adaptor for selectively moving the holder axially relative to the adaptor.

* * * * *